US 6,743,257 B2

(12) United States Patent
Castro

(10) Patent No.: US 6,743,257 B2
(45) Date of Patent: Jun. 1, 2004

(54) DYNAMIC IMPLANTED INTERVERTEBRAL SPACER

(75) Inventor: Salvatore Castro, Milford, MA (US)

(73) Assignee: Cortek, Inc., Dedham, MA (US)

( * ) Notice: Subject to any disclaimer, the term of this patent is extended or adjusted under 35 U.S.C. 154(b) by 19 days.

(21) Appl. No.: 09/988,931

(22) Filed: Nov. 21, 2001

(65) Prior Publication Data
US 2002/0077702 A1 Jun. 20, 2002

Related U.S. Application Data
(60) Provisional application No. 60/256,632, filed on Dec. 19, 2000.

(51) Int. Cl.⁷ .................................................. A61F 2/44
(52) U.S. Cl. ................................................... 623/17.16
(58) Field of Search ........................ 623/17.11, 17.13, 623/17.15, 17.16, 17.12, 17.14, 16.11, 11.11

(56) References Cited

U.S. PATENT DOCUMENTS

| 3,867,728 | A | | 2/1975 | Stubstad |
| 3,875,595 | A | | 4/1975 | Froning |
| 4,309,777 | A | | 1/1982 | Patil |
| 4,349,921 | A | | 9/1982 | Kuntz |
| 4,599,086 | A | | 7/1986 | Doty |
| 4,946,378 | A | | 8/1990 | Hirayama et al. |
| 5,059,193 | A | * | 10/1991 | Kuslich .................. 606/61 |
| 5,320,644 | A | * | 6/1994 | Baumgartner .......... 623/17.16 |
| 5,390,683 | A | * | 2/1995 | Pisharodi ................. 128/898 |
| 5,470,230 | A | * | 11/1995 | Daftary et al. .......... 433/174 |
| 5,534,029 | A | | 7/1996 | Shima |
| 5,554,191 | A | * | 9/1996 | Lahille et al. ............. 623/17 |
| 5,645,599 | A | * | 7/1997 | Samani .................... 623/17 |
| 5,674,294 | A | * | 10/1997 | Bainville et al. .......... 623/17 |
| 5,702,450 | A | * | 12/1997 | Bisserie ................. 623/17.16 |
| 5,725,581 | A | * | 3/1998 | Branemark ............... 623/16 |
| 5,782,865 | A | * | 7/1998 | Grotz ..................... 606/232 |
| 5,824,093 | A | * | 10/1998 | Ray et al. .............. 623/17.16 |
| 5,865,848 | A | | 2/1999 | Baker |
| 5,888,222 | A | | 3/1999 | Coates et al. |
| 5,888,223 | A | | 3/1999 | Bray, Jr. |
| 5,899,941 | A | | 5/1999 | Nishijima et al. |
| 5,984,922 | A | | 11/1999 | McKay |
| 5,989,291 | A | | 11/1999 | Ralph et al. |
| 6,001,130 | A | | 12/1999 | Bryan et al. |
| 6,019,793 | A | * | 2/2000 | Perren et al. .............. 623/17 |
| 6,039,762 | A | | 3/2000 | McKay |
| 6,086,613 | A | | 7/2000 | Camino et al. |
| 6,129,763 | A | * | 10/2000 | Chauvin et al. ........... 623/17 |
| 6,132,465 | A | * | 10/2000 | Ray et al. .............. 623/17.16 |
| 6,280,475 | B1 | * | 8/2001 | Bao et al. .............. 623/17.16 |
| 6,395,031 | B1 | * | 5/2002 | Foley et al. ............ 623/17.11 |
| 6,409,766 | B1 | * | 6/2002 | Brett ..................... 623/17.16 |
| 2002/0049497 | A1 | * | 4/2002 | Mason ................... 623/17.11 |

* cited by examiner

Primary Examiner—Eduardo C. Robert
(74) Attorney, Agent, or Firm—Burns & Levinson LLP; Trevor D. Arnold; Frederick C. Williams

(57) ABSTRACT

The invention is a single piece, self seating and locking dynamic intervertebral spacer. The dynamic spacer is load-supporting but also able to undergo flexure in either or both the lateral and sagittal planes.

9 Claims, 5 Drawing Sheets

DYNAMIC IMPLANTED INTERVERTEBRAL SPACER

PRIORITY

This application is related to and claims priority from the U.S. Provisional Application No. 60/256,632, filed Dec. 19, 2000.

FIELD OF THE INVENTION

The present invention relates to implants for repair of spinal defects and injuries. It relates in particular to implants having utility to maintain intervertebral spacing after disc removal. It further relates to intervertebral spacers which can permit at least some remaining spinal flexibility.

BACKGROUND OF THE INVENTION

Natural intervertebral spinal discs serve multiple purposes. The first, and perhaps most basic, is to preserve the anatomical spacing between adjacent vertebrae such that the spinal column and horizontally branching nerve bundles are allowed to function normally. A second major purpose is to allow relative flexural motion between adjacent vertebral bodies. Natural flexibility, at least of the upper spine, permits rotation about two horizontal axes and one vertical axis. Finally, the disc also serves as a shock absorber for columnar loading of the spine. However, mechanical trauma, degenerative disc disease, and other pathogenesis can compromise a disc's ability to maintain the spacing, facilitate flexibility, and provide the shock absorbing function.

One option after the surgical removal of a damaged disc might be to allow the intervertebral space to collapse. Collapse, however, usually causes compressive damage to the spinal cord and the associated nerve bundles. Also, the intervertebral space may fill with scar tissue that can aggravate nerve damage. Thus the simple removal of a damaged disc, without providing for maintenance of the normal vertebral spacing is undesirable.

Discectomy therefore is usually supplemented by (1) rigid fusion of the adjacent vertebrae with new bone growth; (2) application of rigid nonfusing hardware; or (3) insertion of an artificial disc. As the patent literature shows, these approaches have been tried in many variations but have significant disadvantages.

a. Vertebral Fusion

Well-known to those skilled in the art is interbody fusion wherein the disc is partially or wholly excised and living bone or various forms of calcium phosphate or other substrate material is placed within the space previously occupied by the disc for the purpose of restoring the normal separation, strength, and stability. Fusion is intended to provide healthy, living bone between the adjacent vertebrae.

For fusion to occur within the disc space, it is frequently necessary to prepare the adjacent vertebrae by excising portions of the cortical exterior surfaces, usually of the vertebral endplates so as to allow an interposed bone graft to come into direct contact with the cancellous (and vascularized) interior of the vertebrae.

Historically, two types of bone grafts have been available for anterior cervical fusion. One type is a round dowel plug-like configuration, such as the original Cloward dowel. The second type, a rectangular plug in a rectangular hole, is often referred to as the Smith-Robinson technique. The bone can be obtained from the patient's own iliac crest, from allograft cadaveric crest, or cut from a hard femoral cortical bone.

Both techniques can have disadvantages. For example, the dowel approach frequently flattens the intervertebral space, causing it to induce an undesirable kink in the natural lordosis. Also, the instrumentation used to implant the dowel is bulky and tends to be difficult to use. Thus many surgeons have abandoned this technique. The Smith-Robinson approach has problems because lack of preparation of the endplates leads to non-incorporation and eventual collapse. Moreover, the use of autograft bone to fill the disc space is often less than optimal since it requires an additional incision and healing and is of limited availability in its most useful form.

b. Artificial Discs

Extensive research has been devoted to developing an effective artificial disc. No such device has yet been found that is medically acceptable. Examples of various prosthetic or artificial disc attempts include Fassio, U.S. Pat. No. 2,372,622; Stubstad, U.S. Pat. No. 3,867,728; Froning, U.S. Pat. No. 3,875,595; Patil, U.S. Pat. No. 4,309,777; Kuntz, U.S. Pat. No. 4,349,921; Hirayama, et al., U.S. Pat. No. 4,946,378; Nishijima, et al., U.S. Pat. No. 5,899,941; Bryan, et al., U.S. Pat. No. 6,001,130. Substantial numbers of others exist.

c. Spacers

A number of intervertebral spacers designed for installation between adjacent vertebrae have been patented. These include: U.S. Pat. No. 6,086,613 to CAMINO, et al., relates to intervertebral spacers used in connection with spinal fusion. U.S. Pat. No. 6,039,762 to McKay describes a spacer body having an outer surface and a height approximating the height of a human disc space, said body composed of a porous, biocompatible ceramic material for permitting tissue ingrowth therethrough. U.S. Pat. No. 5,989,291 to RALPH, et al. describes an intervertebral spacer having a pair of opposing plates for seating against opposing vertebral bone surfaces, separated by at least one spring mechanism. In a first embodiment there are two Belleville washers which are oriented in opposite directions such that the narrow ends thereof are in contact with each other and the wider ends are in contact with the respective end plates. The Belleville washers work as springs. (Belleville washers are described as frustoconical in shape.)

U.S. Pat. No. 5,984,922 to McKay describes a spinal fixation device consisting of an intervertebral body wedge which is inserted between vertebral bodies by sequentially expanding the disc space using a spacer. No posterior fixation devices are needed for stabilization of the vertebrae. U.S. Pat. No. 5,888,222 to COATES, et al. describes a spinal spacer that engages adjacent vertebrae. The spacer includes a body having two ends, at least one of which "defines" an inferior vertebral engaging surface having a set of migration resistance grooves. U.S. Pat. No. 5,534,029 to Shia discloses an articulated vertebral body spacer consisting of a pair of upper and lower joint pieces to be inserted between vertebrae. This spacer allows its components to pivot in accordance with forward/backward and bending motions of vertebral bodies. U.S. Pat. No. 4,599,086 to Dogy discloses a spinal stabilization device positionable between separated but neighboring vertebrae. A wrench can be inserted into the opening until it engages a pair of pins, and then the wrench can be rotated to advance the pins into the abutting vertebral bodies.

Two spacer inventions that are designed specifically for use in connection with subsequent fusion processes are: U.S. Pat. No. 5,888,223 to BRAY, Jr., which discloses an anterior fixation device consisting of an oval shaped hollow intervertebral spacer and a retaining plate. The spacer has a side wall and superior and inferior walls. The superior and inferior walls are dome-shaped and porous to allow bone to grow through the device to achieve fusion of two adjacent vertebral bodies; and U.S. Pat. No. 5,865,848 to Baker describing a spinal fusion implant assembly for spacing vertebrae. The device includes a translation mechanism for providing relative motion between the components.

An additional area of prior art includes all devices designed to be applied to one or more exterior surfaces of the spine. Such devices include all types of plates, struts, and rods which are attached by hooks, wires and screws. Other devices are simply variations on the use of rods (e.g. Harrington, Luque, Cotrel-Dubosset, Zielke), wires or cables (Dwyer), plates and screws (Steffee), or struts (Dunn, Knowles).

A preferable spacer would at least to some extent preserve the ability of the patient to rotate portions of the spinal column about two perpendicular horizontal axes (and linear combinations thereof) and about the vertical axis. All of the prior art approaches suffer from the drawback that they either do not attempt to preserve such flexibility or they are unable in practice to achieve a workable device. In addition they suffer from other drawbacks.

The principal drawbacks of the fusion approach are that until very recently the success rate, that is, actual achievement of fusion, has been very modest. Secondly, in cervical as opposed to lumbar application, the diminution in mobility of the spine about rotational axes is a much more significant lasting effect for the patient.

The principal aim of artificial discs has been to provide a prosthesis which preserves as much of the patient's prior ability to move as possible. The principal drawback of artificial discs is that they simply do not work in a medical sense.

Spacers have the drawback that, by themselves, they do not achieve the beneficial results of fusion. On the other hand, most of them are rigid, and therefore also have the same drawback as successful fusion, namely reducing the patient's flexibility.

OBJECTS OF THE INVENTION

Accordingly, it is an object of the present invention to provide a single-piece intervertebral implant that can serve as a spacer between adjacent cervical vertebrae. Another object of the invention is to provide an intervertebral implant that allows relative motion of the adjacent vertebral bodies. Another object of the present invention is to provide a low cost intervertebral implant that is small enough to allow rapid and easy anterior or posterior installation into either the cervical or the lumbar regions of the spine. Another object of the present invention is to provide an intervertebral implant device that is self-adhering upon installation. Another object of the present invention is to provide an intervertebral implant device that can maintain intimate, grasping adherence with the vertebral bodies, even when loaded in tension. Another object of the present invention is to provide an artificial disc prosthesis able to allow for full bending movement of the two vertebral bodies between which it is installed, allowing flexibility within both the lateral and sagittal planes. Yet another object of the present invention is to provide an intervertebral implant device that can pierce the bony cortex of the vertebral bodied during installation. And yet a further object of the present invention is to provide an intervertebral implant device that provides self-centering alignment upon installation.

Additional objects of the invention are to provide a single-piece spacer device which alone, or with a second such spacer device, can serve as a spacer between adjacent vertebra within the lumbar region of the spine as part of a vertebral fusion process. Yet another object of the present invention is to provide an intervertebral implant device that provides the correct amount of loading in order to promote bone growth and vertebral fusion A final object of the invention is to provide a single-piece device which alone in the cervical region of the spine or in combination with a second like device in the lumbar region of the spine can be driven into an intervertebral space with a single force-applying operation for each of the one or two devices.

SUMMARY OF THE INVENTION

The present invention is an implantable intervertebral spacer designed to both preserve the space between adjacent vertebrae and to provide some continued spinal flexibility by virtue of its flexible construction. This spacer is also characterized by single piece construction and by the property of being self guiding upon initial insertion into the intervertebral space. This invention also has four spaced-apart tail pieces flexibly linked to one another, consisting of one upper set of two horizontally spaced-apart tail pieces and one lower set of two horizontally spaced-apart tail pieces, the upper and lower sets also being vertically spaced-apart from one another. Each of the two upper spaced-apart elongated tail pieces is independently flexibly linked to each of the corresponding spaced apart elongated lower tail pieces. Each of the tail pieces also comprises an elongated post supporting a bone gripping barb and a cutting edge having an inwardly angled facet. Upon installation between adjacent vertebral bodies, the implant is self locking by virtue of strain induced in the elongated barb-supporting posts. The device is implantable as a single unit within the intervertebral space between adjacent cervical vertebrae or it is implantable in conjunction with a second spacer within the same intervertebral space. Because of the cutting edges and barbs, it is implanted by being impacted with a driver device, at which point it is firmly seated and will not pull or creep out. The device also has a wedge shaped front portion to guide it into the desired position during installation. The bone gripping induced strain manifests within each of the elongated posts supporting each barb of each spaced-apart pair of barbs when the facet causes inward bending strain of the elongated posts upon installation into the vertebral bone.

The present invention is an implantable intervertebral device that can be configured also to promote bone growth and vertebral fusion. The vertical slot between the upper and lower sets of the two horizontally spaced-apart tail pieces can be loaded with bone graft material and/or bone morphogenic protein so as to create a fusion column and promote intervertebral fusion. It is known that compressive loading of graft material promotes new bone growth and healing. (This principle is generally referred to as Wolff's law.) The horizontal slot between the upper and lower sets of tail pieces can be varied in height, and the radius of the internal void in the portion connecting the upper part of the device to the lower part of the device can be varied, both so as to provide flexing sufficient to produce enough loading on the graft material to promote bone growth and vertebral fusion while still providing sufficient compressive strength to maintain the necessary intervertebral spacing.

The spacer of the current invention can be fabricated from metal, preferably titanium or stainless steel. Or it can be fabricated from organic polymer such as thermoplastic or thermosetting plastic unfilled or filled with fibers such as glass, metal or carbon. Preferably, said implant spacer, if fabricated from organic polymer, is to be fabricated from polyether ether ketone (PEEK), most preferably filled with fibers of metal or glass or, most preferably, carbon.

A second embodiment of the said cervical\lumbar implant spacer employs the use of bullets situated upon elongated posts instead of barbs as a way to grip the vertebral bone. The forward cutting edge of each bullet has an angled facet that causes induced strain to arise within the elongated support post during installation.

Figure 1:
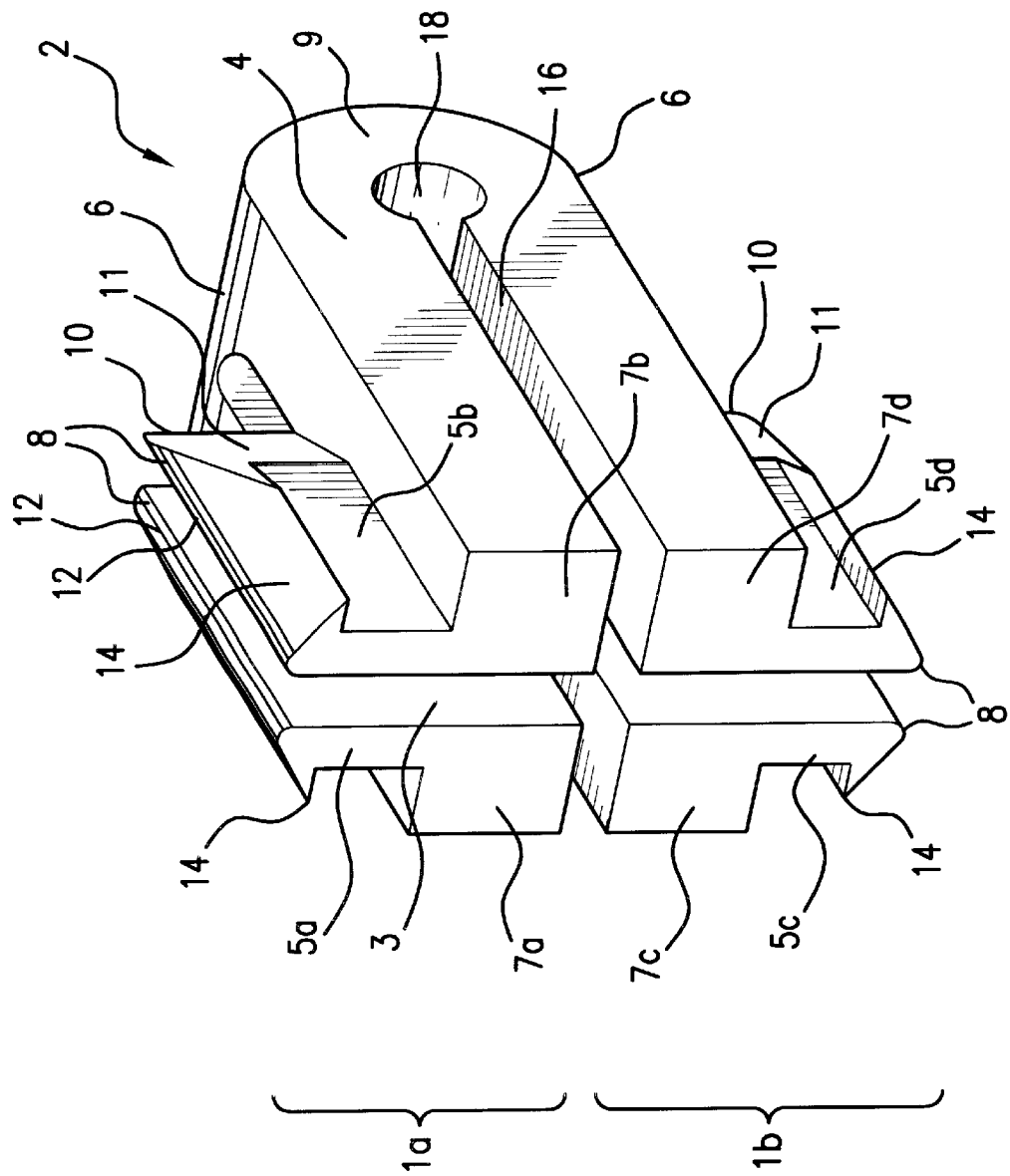
FIG. 1 is an oblique view of the cervical/lumbar implant spacer.
Figure 2B:
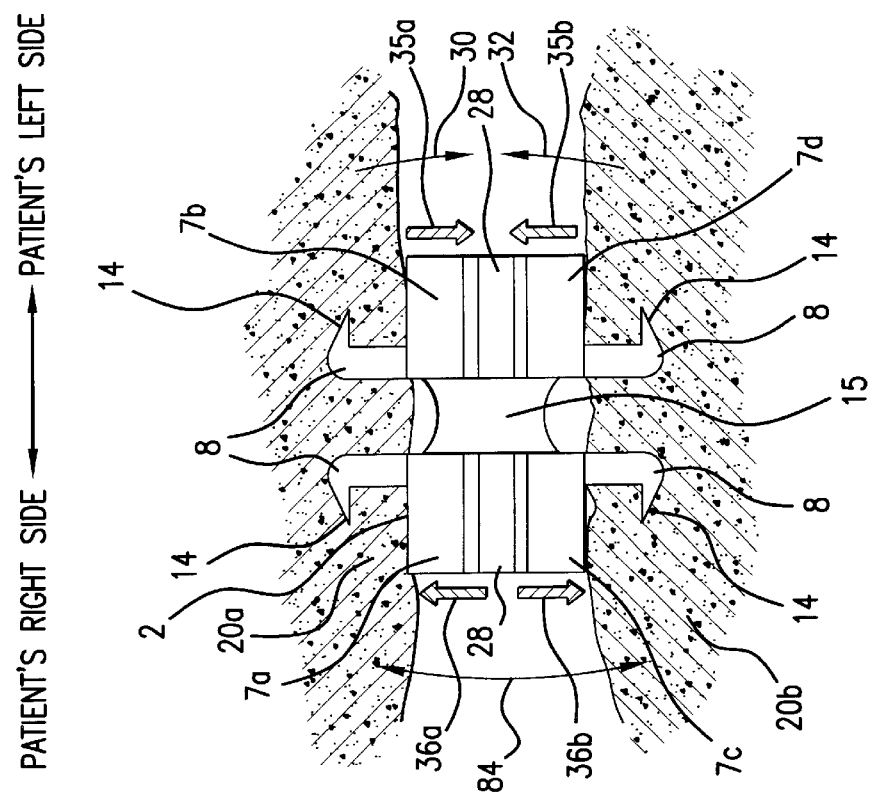
FIG. 2B is a sagittal orthogonal view of a single cervical/lumbar spacer inserted between two vertebrae.
Figure 2A:
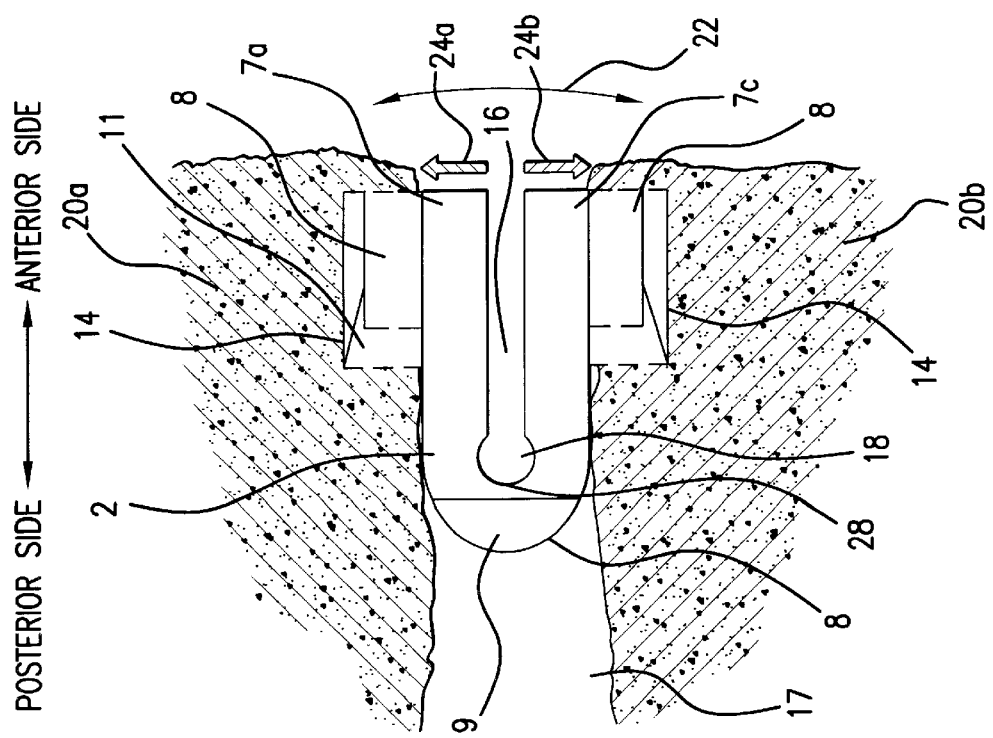
FIG. 2A is a lateral orthogonal view of a single cervical/lumbar spacer inserted between two vertebrae.
Figure 3A:
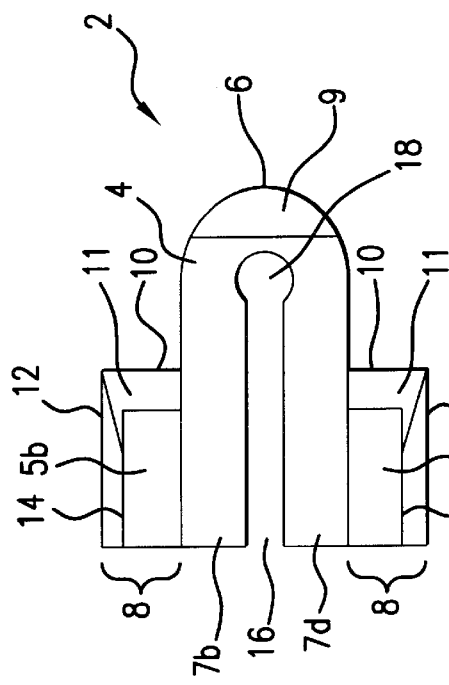
FIG. 3A is a top view of the cervical/lumbar spacer.
Figure 3C:
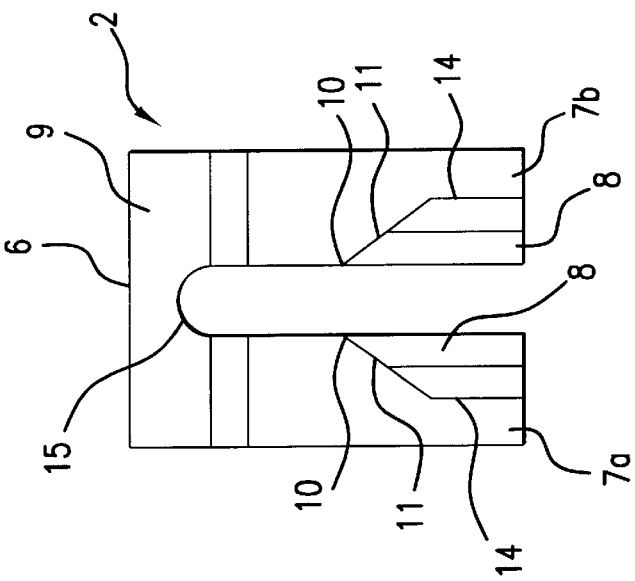
FIG. 3C is a side view of the cervical/lumbar spacer.
Figure 3B:
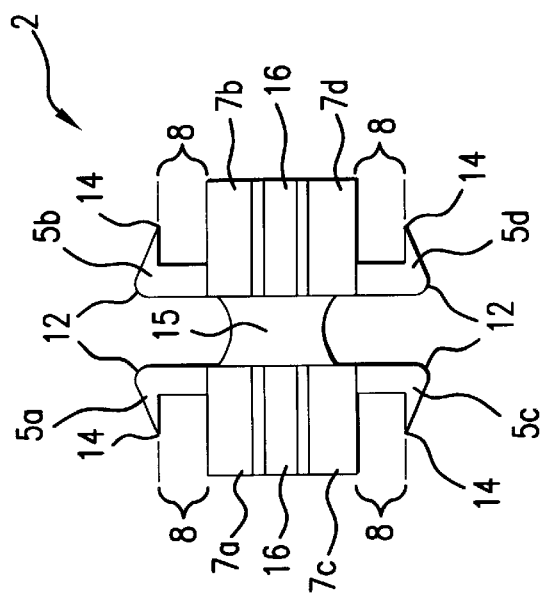
FIG. 3B is a rear view of the cervical/lumbar spacer.
Figure 4:
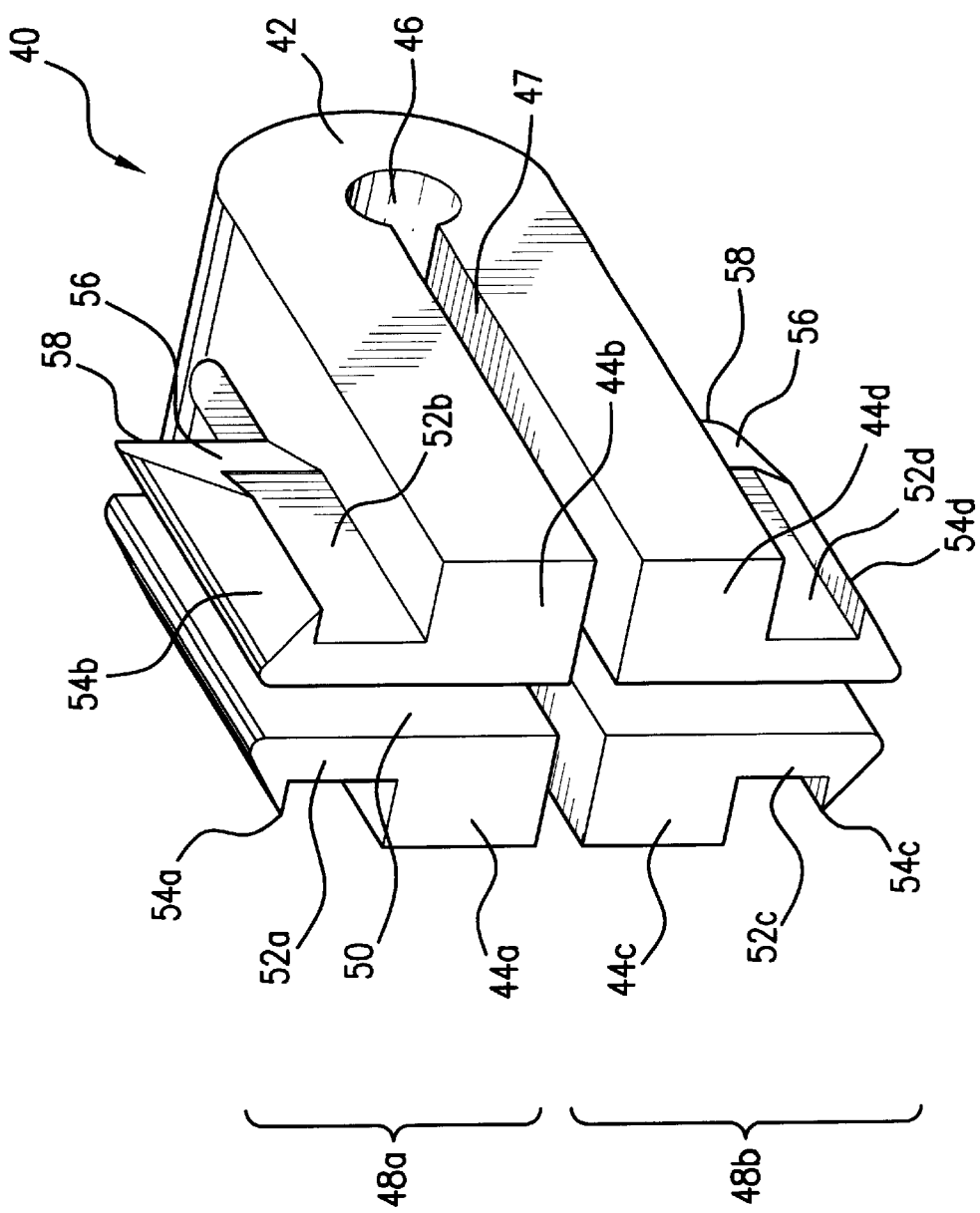
FIG. 4 is an oblique view of one embodiment of the cervical/lumbar implant spacer.
Figure 5:
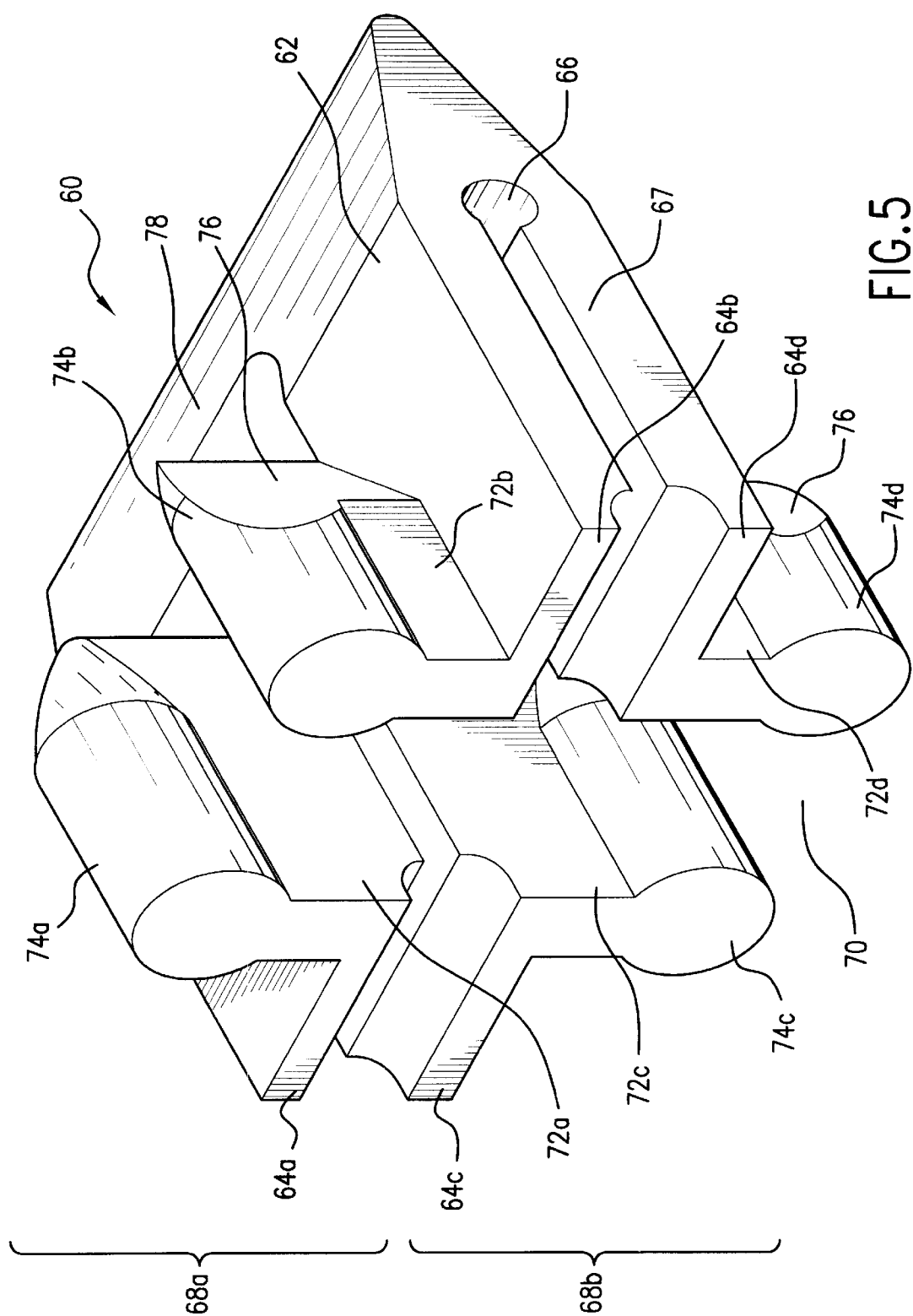
FIG. 5 is an oblique view of a second embodiment of the cervical/lumbar implant spacer.

IDENTIFICATION OF ITEMS IN THE FIGURES
FIG. 1
1a—upper portion
1b—lower portion
2—dynamic cervical/lumbar spacer
3—vertical slot
4—body of spacer
5a,5b,5c,5d—elongated barb support posts (see 8)
6—wedge shaped forward end of spacer
7a,7b,7c,7d—tail pieces of spacer
8—bone gripping latching portion of spacer (see 5x)
9—forward portion of the spacer
10—sharp forward cutting edge of bone gripping latch portion
11—medially inwardly angled facet
12—rounded top side
14—elongated bone engaging barb
16—horizontal slot between tail pieces
18—stress relieving region
FIG. 2A
2—dynamic cervical/lumbar spacer
7a,7c—tail pieces of spacer
8—bone gripping latching portion of spacer
9—forward portion of the spacer
11—medially inwardly angled facet
14—elongated bone engaging barb
16—horizontal slot between tail pieces
17—intervertebral space
18—stress relieving region
20a—anterior side of vertebral body
20b—anterior side of vertebral body
22—motion indicating two headed arrow (vertebral)
24a,24b—motion-indicating little arrows (spacer)
28—flexural fulcrum region
FIG. 2B
2—dynamic cervical/lumbar spacer
7a,7b,7c,7d—tail pieces of spacer
8—bone gripping latching portion of spacer
14—elongated bone engaging barb
15—stress relieving lateral flexure region
20a—anterior side of vertebral body
20b—anterior side of vertebral body
28—flexural fulcrum region
30,32—motion indicating arrows (vertebral)
34—motion indicating two headed arrow (vertebral)
35a,35b—motion-indicating little arrows (spacer)
36a,36b—motion-indicating little arrows (spacer)
FIG. 3A
2—dynamic cervical/lumbar spacer
4—body of spacer
5a, 5b, 5c, 5d—elongated barb support posts
6—wedge shaped forward end of spacer
7b,7d—tail pieces of spacer
8—bone gripping latching portion of spacer
9—forward portion of the spacer
10—sharp forward cutting edge of bone gripping latch portion
11—medially inwardly angled facet
12—rounded top side
14—elongated bone engaging barb
16—slot between tail pieces
18—stress relieving region
FIG. 3B
2—dynamic cervical/lumbar spacer
5a, 5b, 5c, 5d—elongated barb support posts
7a,7b,7c,7d—tail pieces of spacer
8—bone gripping latching portion of spacer
12—rounded top side
14—elongated bone engaging barb
15—stress relieving lateral flexure region
16—horizontal slot between tail pieces
FIG. 3C
2—dynamic cervical/lumbar spacer
6—wedge shaped forward end of spacer
7a,7b—tail pieces of spacer
8—bone gripping latching portion of spacer
9—forward portion of the spacer
10—sharp forward cutting edge of bone gripping latch portion
11—medially inwardly angled facet
14—elongated bone engaging barb
15—stress relieving lateral flexure region
FIG. 4
40—first embodiment of the dynamic lumbar/cervical spacer
42—wedge shaped front portion
44a,44b,44c,44d—spaced apart elongated tail pieces
46—strain relieving circular region
47—slot separating upper and lower tail piece pairs.
48a,48b—upper and lower portions of spacer 40
50—juncture slot separating the tail pieces
52a,52b,52c,52d—elongated support posts
54a,54b,54c,54d—elongated barbs
56—facets
58—sharp forward cutting edge
FIG. 5
60—second embodiment of the dynamic lumbar/cervical spacer
62—wedge shaped front portion
64a,64b,64c,64d—spaced apart elongated tail pieces
66—strain relieving circular region
67—slot separating upper and lower tail piece pairs.
68a,68b—upper and lower portions of spacer 60
70—juncture slot separating the tail pieces
72a,72b,72c,72d—elongated support posts
74a,74b,74c,74d—elongated bullets
76—facets
78—sharp forward cutting edge

DESCRIPTION OF THE PREFERRED EMBODIMENTS

The present invention, known as the dynamic lumbar/cervical spacer, is an intervertebral implant device designed to perform one or a combination of three basic functions: (1) vertebral spacer; (2) spacer to be used in conjunction with vertebral fusion; and (3) artificial disc.

The said dynamic spacer is of single piece construction. It is self guiding upon initial insertion into the intervertebral space, and it is self locking upon installation between adjacent vertebral bodies. It is dynamic in the sense that it is designed to be flexible within both the sagittal and lateral planes; that is, subsequent to installation, the patient will be able to move in such a way that the vertebrae between which the spacer has been installed will be able to have some or all of the motions allowed by a natural and healthy intervertebral disc.

The dynamic spacer is provided with a pair of spaced apart cutting edges on the spacer's upper face and a similar pair of cutting edges on the spacer's lower face. The respective pairs of spaced apart cutting edges enable the spacer to cut into the adjacent vertebral bodies upon being driven into the intervertebral disc space. Each of the said cutting edges is furthermore provided with either "barbs" or "bullets" that inhibit subsequent movement or pullout of the spacer away from the vertebrae into which it has been driven. In addition, each pair of cutting edges is geometrically arranged upon an elongated post so as to provide a grasping force, through induced strain within the elongated posts so as to hold the spacer within intimate contact with each respective vertebra to which it is attached.

The dynamic vertebral spacer of the present invention is designed to be installable by being impacted or otherwise driven or forced into place with a driver device. The said spacer is also designed to be manufactured in a multiplicity of sizes and a multiplicity of proportions of length, width and height so as to accommodate a variety of intervertebral spacings and vertebral body sizes according to the needs of the patient.

The dynamic spacer is designed to also promote bone growth and intervertebral fusion. The vertical slot between the upper and lower sets of the two horizontally spaced-apart tail pieces can be configures so that it can be loaded with graft to create a fusion column and promote fusion. The horizontal slot between the upper and lower sets of tail pieces can be varied in height, and the radius of the inner void in the portion of the implant connecting the upper portions of the spacer to the lower portions of the spacer can also be varied, so as to provide enough flexing to produce loading on the graft sufficient to promote bone growth and vertebral fusion while also providing compressive strength sufficient to maintain the required separation of the adjacent vertebrae.

Referring now to FIG. 1, there is shown in oblique view one embodiment of a single dynamic cervical/lumbar spacer 2 according to the present invention. The spacer 2 consists of a single piece body 4 having a wedge shaped front end 6 and four elongated tail pieces 7a, 7b, 7c and 7d flexibly attached to one another by way of the wedge shaped front end 6 located in the forward portion 9 of the spacer. Each of the elongated tail pieces 7a, 7b, 7c and 7d has contiguous with it a bone gripping latching portion 8 consisting of an elongated post 5a, 5b, 5c, 5d upon each of which is disposed a sharp forward cutting edge 10 having a medially inwardly angled facet 11, a rounded top side 12 and an elongated bone engaging barb 14.

FIGS. 2A and 2B are orthogonal views of a single dynamic spacer according to the present invention inserted between the anterior portions of two vertebral bodies 20a, 20b. The bone grabbing latching portions 8 of the spacer 2 are shown embedded within the adjacent vertebral bodies 20a, 20b. The dynamic features of the dynamic spacer 2 will become evident upon examination of the following additional FIGURES.

FIGS. 3A, 3B and 3C show three orthogonal views of the dynamic spacer 2 shown in FIG. 1. FIG. 3A is a side view of the spacer 2 showing the single piece body 4 with the wedge shaped front end 6 and two of the four spaced apart and elongated tail pieces 7b, 7d separated from one another by the slot 16 and flexibly attached to one another by way of the wedge shaped front end 6. The slot 16 terminates in the stress relieving circular portion 18 near the front region 6 of the spacer. The bone gripping latching portions 8 are shown in FIG. 3A being contiguous with the sharp forward cutting edge 10 and the medially inwardly angled facet 11 and the elongated bone engaging barb 14. More specifically, each bone latching portion 8 consists of an elongated support post 5a, 5b, 5c or 5d upon which is disposed the elongated bone engaging barb 14 having a forward cutting edge 10 with an angled facet 11.

Contemplation of the FIGS. 3A, 3B and 3C will reveal to those skilled in the mechanical arts the dynamic aspect of the present vertebral spacer invention. In particular, in FIG. 3B, the respective elongated tail pieces 7a,7b,7c,7d are able to move flexurally in relation to one another. For example, and referring to FIGS. 2A, 2B the spacer 2 is shown after having been inserted into the intervertebral space 17, by being forced in or driven in by impact. During the insertion process, the four medially inwardly directed facets 11 of the bone gripping portions 8 engage the cortex bone the vertebral bodies 20a, 20b in such as way as to force medially inwards, towards one another, the respective pairs of spaced apart elongated posts 5a, 5b and 5c, 5d such that induced strain in the elongated posts, as well as in the region 15 between the respective pairs of elongated tail pieces 7a,7c and 7b,7d, forces the elongated barbs 14 into intimate gripping contact with the vertebral bone.

During installation, flexure of the region 15 necessarily forces together the respective pairs of tail pieces 7a,7c and 7b,7d, but primarily induces gripping strain in the respective pairs of elongated posts 5a, 5c and 5b, 5d. As a result, the induced strain produces a laterally outwardly directed force that causes the elongated bone engaging barbs 14 to maintain in intimate contact with the vertebral bone. The inventor recognizes that the vertical portions of the bone gripping latching portions 8 also undergo a small degree of flexure and thereby also have an induced strain that serves to secure the spacer 2 in intimate contact with the vertebral bodies 20a, 20b.

The dynamic aspects of the dynamic lumbar/cervical spacer are yet further evident within the context of FIGS. 2A and 2B, which show the spacer 2 implanted between the two vertebrae 20a, 20b. FIG. 2A shows the spacer 2 located more or less within the sagittal plane, with said the spacer being close to the anterior side of the vertebral bodies. Note the two-headed curved arrow 22, indicating relative motion of the two vertebral bodies, such motion being of the sort arising between vertebrae when the patient moves in such a way as corresponds to an arching of the back, i.e., bending backwards. Such increasing separation of the anterior sides of the respective vertebral bodies 20a, 20b can be accommodated by the dynamic spacer 2 in that the elongated tail pieces 7a,7c (and 7b,7d, not shown) can flex apart from one another about the fulcrum 28 within the circular stress-relieving region 18 located in the forward portion 9 of the spacer. The flexure of the tail pieces 7a,7c is indicated by the small arrows 24,26. It is important to note that during spinal flexure of the sort causing increasing separation of the vertebral bodies 20a, 20b that the bone gripping latching portions 8 remain tightly in contact with the respective vertebral bodies, according to the design function of the elongated bone engaging barbs 14.

Correspondingly, when the patient's spine is flexed in the opposite direction, as during a forward bending motion, the space between the anterior sides of the vertebral bodies 20a, 20b shown in FIG. 2A decreases. Under such conditions, the two-headed arrow 22 would be reversed so as to indicate a coming together of the vertebral bodies. Likewise, the tail pieces, 7a,7c would also be forced into closer proximity about the fulcrum 28, and the orientation of the small motion indicating arrows 24a,24b would be reversed from that shown in FIG. 2A. In FIG. 2B, the fulcrum 28 can be seen to be a line (dotted) along the forwardmost side of the stress relieving region 18. (NOTE: In more specific point of fact, the line denoted by the callout number 28 in FIG. 2B designates a zone of tension or compression as the whole forward region 9 of the spacer flexes in respective response to the increasing or decreasing separation of the upper tail pieces 7a,7b from the lower tail pieces 7c, 7d.).

Further details of the dynamic properties of the vertebral spacer 2 according to the present invention are illustrated in FIG. 2B, which is a view of the implanted spacer from the anterior side of the spine, i.e., looking toward it from the front of the patient's body. The pair of curved arrows 30,32 and the single two-headed arrow 34 illustrate the relative motion of the two vertebral bodies 20a, 20b if the patient were to bend laterally (specifically toward the patient's left side). As viewed in FIG. 2B, the right side of the vertebral bodies 20a, 20b become closer while the left side of the bodies move farther apart. The spacer 2 is able to accommodate such motion because the tail pieces 7b, 7d on the right side of the FIGURE can flex into closer proximity, due to compression, while the tail pieces 7a, 7c on the left side move farther apart, due to tension. In both instances, compression or tension, the relative motions of the respective pairs of tail pieces 7a, 7c and 7b, 7d is associated with flexure about the fulcrum region 28 located within the stress relieving region 18 of the forward region 9 of the spacer.

Embodiment #1

FIG. 4 shows in oblique view a first embodiment of the dynamic lumbar/cervical spacer 40 according to the present invention. The spacer 40 is of single-piece construction. It consists of a wedge shaped front portion 42 and an upper set of two spaced apart elongated tail pieces 44a, 44b and a lower set of two spaced apart elongated tail pieces 44c, 44d. Each of the upper pair of spaced apart tail pieces 44a, 44b are independently flexibly linked to each of the corresponding spaced apart lower tail pieces 44c, 44d respectively. The flexible link between the respective spaced apart upper tail pieces 44a, 44b and the corresponding lower tail pieces 44c, 44d is the front portion 42 containing a stress relieving circular region 46 at the forward end portion of the slot 47 separating the respective upper and lower pairs of tail pieces. The upper portion 48a and lower portion 48b of the spacer 40 are symmetrical with one another about the horizontal plane defined by the plane of the slot 47. Each of the two elongated upper tail pieces 44a, 44b is able to move in the vertical direction, independently of the other, in relation to each of the corresponding two lower tail pieces 44c, 44d, thereby affording movement between the vertebrae (20a, 20b in FIGS. 2A, 2B) in both the lateral and the sagittal planes.

On the top of the upper portion 44a, disposed in a bilaterally symmetric way about the vertical plane defined by the juncture slot 50 separating the left tail pieces 44a, 44c from the right tail pieces 44b, 44d, are two elongated posts 52a, 52c. Each of the two elongated posts 52a, 52c is topped by an elongated barb 54a, 54c. Corresponding elongated barbs 54b, 54d are disposed on the lower portion 44b of the spacer 40. Facets 56 are disposed at the forward end of each elongated post and barb set, providing a sharp forward cutting edge 58 at the forward end of each of the four post and barb sets. Each of the four facets 56 (only two are shown in the FIGURE) is angled in such a way that when the spacer 40 is forced between the vertebral bodies (20a, 20b in FIGS. 2A, 2B), the upper set of elongated posts 52a, 52b and the lower sets of elongated posts 52c, 52d are forced medially toward one another in such a way that strain is induced in the respective elongated posts so as to facilitate the ability of the elongated barbs 54a, 54b, 54c, 54d to remain in continuing firm contact with the vertebral bone (not shown in FIG. 4). As should be apparent to those skilled in the art, a portion of medially directed strain in each set of the elongated posts 52a, 52b and 52c, 52d is born by the respective tail pieces 44a through 44d.

Embodiment #2

FIG. 5 shows in oblique view a second embodiment of the dynamic lumbar/cervical spacer 60 according to the present invention. The spacer 60 is of single-piece construction. It consists of a wedge shaped front portion 62 and an upper set of two spaced apart elongated tail pieces 64a, 64b and a lower set of two spaced apart elongated tail pieces 64c, 64d. Each of the upper pair of spaced apart tail pieces 64a, 64b are independently flexibly linked to each of the corresponding spaced apart lower tail pieces 64c, 64d respectively. The flexible link between the respective spaced apart upper tail pieces 64a, 64b and the corresponding lower tail pieces 64c, 64d is the front portion 62 containing a stress relieving circular region 66 at the forward end portion of the slot 67 separating the respective upper and lower pairs of tail pieces. The upper portion 68a and lower portion 68b of the spacer 60 are symmetrical with one another about the horizontal plane defined by the plane of the slot 67. Each of the two elongated upper tail pieces 64a, 64b is able to move in the vertical direction, independently of the other, in relation to each of the corresponding two lower tail pieces 64c, 64d, thereby affording movement between the vertebrae (20a, 20b in FIGS. 2A, 2B) in both the lateral and the sagittal planes.

On the top of the upper portion 68a, disposed in a bilaterally symmetric way about the vertical plane defined by the juncture slot 70 separating the left tail pieces 64a, 64c from the right tail pieces 64b, 64d, are two elongated posts 72a, 72c. Each of the two elongated posts 72a, 72c is topped by an elongated bullet 74a, 74c. Corresponding elongated bullets 74b, 74d are disposed on the lower portion 68b of the spacer 60. Facets 76 are disposed at the forward end of each elongated post and bullet set, providing a sharp forward cutting edge 78 at the forward end of each of the four post and bullet sets. Each of the four facets 76 (only two are shown in the FIGURE) is angled in such a way that when the spacer 60 is forced between the vertebral bodies (20a, 20b in FIGS. 2A, 2B), the upper set of elongated posts 72a, 72b and the lower sets of elongated posts 72c, 72d are forced medially toward one another in such a way that strain is induced in the respective elongated posts so as to facilitate the ability of the elongated bullets 74a, 74b, 74c, 74d to remain in continuing firm contact with the vertebral bone (not shown in FIG. 5). As should be apparent to those skilled in the art, a portion of medially directed strain in each set of the elongated posts 72a, 72b and 72c, 72d is born by the respective tail pieces 64a through 64d.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

I claim:

1. An implantable dynamic intervertebral spacer of single piece construction configured to be flexible in a sagital and in a lateral plane after being implanted between two adjacent vertebrae, said spacer having a body comprising a plurality of upper tail pieces and a plurality of lower tail pieces, each of the plural upper tail pieces and each of the plural lower tail pieces additionally comprising a barb support post, each of the barb support posts additionally comprising an elongated bone engaging barb, each of said bone engaging barbs additionally comprising a medially inwardly angled facet.

2. The spacer of claim 1 in which each of said elongated bone engaging barbs additionally comprises a bone gripping latching portion.

3. An implantable dynamic intervertebral spacer of single piece construction configured to be flexible in a sagital and in a lateral plane after being implanted between two adjacent vertebrae, said spacer having a body comprising two upper tail pieces and two lower tail pieces, each of the two upper tail pieces and each of the two lower tail pieces additionally comprising a barb support post, each of the barb support posts additionally comprising an elongated bone engaging barb, each of said bone engaging barbs additionally comprising a medially inwardly angled facet.

4. The spacer of claim 3 in which each of said elongated bone engaging barbs additionally comprises a bone gripping latching portion.

5. An implantable dynamic intervertebral spacer of single piece construction configured to be flexible in a sagital and in a lateral plane after being implanted between two adjacent vertebrae, said spacer having a body comprising a plurality of upper tail pieces and a plurality of lower tail pieces, each of the plural upper tail pieces and each of the plural lower tail pieces additionally comprising a barb support post, each of the barb support posts additionally comprising an elongated bullet configured to engage bone.

6. The spacer of claim 5 in which each of said elongated bullets configured to engage bone additionally comprises a medially inwardly angled facet.

7. An implantable dynamic intervertebral spacer of single piece construction configured to be flexible in a sagital and in a lateral plane after being implanted between two adjacent vertebrae, said spacer having a body comprising two upper tail pieces and two lower tail pieces, each of the two upper tail pieces and each of the two lower tail pieces additionally comprising a barb support post, each of the barb support posts additionally comprising an elongated bullet configured to engage bone.

8. The spacer of claim 7 in which each of said elongated bullets configured to engage bone additionally coniprises a medially inwardly angled facet.

9. An implantable dynamic intervertebral spacer of single piece construction configured to be flexible in a sagital and in a lateral plane after being implanted between two adjacent vertebrae, said spacer having a body comprising two upper tail pieces and two lower tail pieces and a wedge shaped front end that connects the two upper tail pieces and the two lower tail pieces and provides an independently flexible linkage between each of the two upper tail pieces and each of the corresponding two lower tail pieces.

* * * * *